United States Patent
Rico

(10) Patent No.: US 6,375,942 B1
(45) Date of Patent: Apr. 23, 2002

(54) SKIN HEALING OINTMENT

(76) Inventor: Michael C. Rico, 5683 Converse Ct., Hilliard, OH (US) 43026-9585

( * ) Notice: Subject to any disclaimer, the term of this patent is extended or adjusted under 35 U.S.C. 154(b) by 0 days.

(21) Appl. No.: 09/652,382

(22) Filed: Aug. 31, 2000

Related U.S. Application Data

(60) Provisional application No. 60/151,645, filed on Aug. 31, 1999.

(51) Int. Cl.$^7$ .............................................. A61K 31/74
(52) U.S. Cl. ................ 424/78.07; 424/401; 424/78.06; 424/642
(58) Field of Search .............................. 424/401, 78.06, 424/78.07, 642

(56) References Cited

U.S. PATENT DOCUMENTS

| | | | |
|---|---|---|---|
| 4,355,046 A | 10/1982 | Suess | 424/355 |
| 4,454,118 A | 6/1984 | Johnson | 424/95 |
| 4,512,978 A * | 4/1985 | Inwood | 424/145 |
| 4,713,242 A | 12/1987 | Trenzeluk | 424/145 |
| 4,788,061 A | 11/1988 | Shore | 424/448 |
| 4,880,627 A | 11/1989 | Trenzeluk | 424/640 |
| 5,407,670 A * | 4/1995 | Shinault | 424/78.06 |

* cited by examiner

Primary Examiner—Jose G. Dees
Assistant Examiner—Konata M. George
(74) Attorney, Agent, or Firm—David A. Greenlee

(57) ABSTRACT

A skin healing ointment comprises wax, petrolatum, antibiotic, zinc oxide and an anti-itch ingredient in the following proportions:

Wax—0.5–5.0 parts

Petrolatum—4.0–10.0 parts

Antibiotic—0.25–5.0 parts

Zinc oxide—up to 8.0 parts

Anti-itch—up to 0.28 parts.

In its preferred form, the ointment comprises, approximately:

Wax—2.0 parts

Petrolatum—7.0 parts

Antibiotic—0.817 parts

Zinc oxide—0.4 parts

Anti-itch—0.05 parts.

Effective treatment of psoriasis, Fifth disease, chafing, burns, chapped skin and rashes comprises application of the ointment three times daily until symptoms disappear, then once daily to keep the skin supple and prevent reoccurrence.

6 Claims, No Drawings

SKIN HEALING OINTMENT

This application claims the benefit of U.S. Provisional Application No. 60/151/645, filed Aug. 13, 1999.

TECHNICAL FIELD

This invention relates to treatment of skin disorders and, more particularly, to an ointment for treating these disorders.

BACKGROUND OF THE INVENTION

Human skin is frequently subject to inhospitable environmental conditions. Among these are harsh chemicals, temperature extremes, moisture extremes, cuts, bruises, sun burn, natural irritants and rashes (such as poison ivy, oak and sumac), and other diseases, such as psoriasis and Fifth's disease. All of these can, separately or in combination, produce painful and debilitating skin disorders, which include dryness, itching, redness, rashes, bleeding and lesions.

One medical specialty, dermatology, has developed to diagnose and treat these disorders and diseases of the skin. In addition, a multi-billion dollar industry comprising hundreds of companies world-wide, has developed to produce and supply thousands of different types of creams, salves, balms, ointments and medicaments for healing the skin. Most are effective to treat some of the disorders some of the time.

Many creams and ointments have been developed to treat skin disorders. U.S. Pat. No. 4,355,046 discloses a treatment method that moisturizes the skin with a cream containing specially formulated petrolatum, a siloxane solvent, and a microcrystalline wax.

U.S. Pat. No. 4,880,627 discloses a skin treatment mixture, which features use of the extract of the Eupatorium plant, plus sulfathiazole, petrolatum and zinc oxide.

U.S. Pat. No. 4,788,061 further suggests a skin treatment that requires absolute occlusion of the skin damage site for at least three days, preferably by an elastic adhesive bandage, which can optionally include corticosteroid.

These are but a representative few of the mixtures that have been patented, but have not proven completely effective in treating all types of skin disorders, nor have they found widespread commercial success. Many other moisturizers, ointments, soaps and creams are commercially available, but have proven to be of limited effect in treatment of all types of skin disorders.

Many prescription ointments have been developed to treat psoriasis, but none have been found effective. In addition, injectable drugs are being tested as cures for psoriasis. These will be extremely costly, and their side effects have yet to be determined.

I have always been plagued by psoriasis. I have relatives who have similar problems, including rough, red and itching skin. I have tried many prescription ointments and treatments and every over-the-counter treatment I could find. None were effective for a full range of skin ailments, and none were found to effective to counter the effects of psoriasis. I decided that there must be an effective combination of ingredients which could free me from the terrible skin problems plaguing me. I set out to try mixing some readily-available (i.e. without prescription) ingredients for two reasons: 1) availability and 2) low cost. If I could just find the right combination of ingredients, I could make it available to millions of fellow sufferers at very affordable prices, thus enabling even the poorest of people to get relief.

There is a very real need for a skin healing ointment which will effectively treat the redness, itching, dryness, cuts, rashes and lesions which all too often plague people's skin.

There is a need for such an ointment that is available over-the-counter, i.e. without a prescription, and that effectively treats psoriasis.

SUMMARY OF THE INVENTION

It is therefore an object of this invention to provide a skin healing ointment which will effectively treat the redness, itching, dryness, cuts, rashes and lesions which all too often plague people's skin.

It is another object of this invention to provide such an ointment that is available over-the-counter, i.e. without a prescription, and that effectively treats psoriasis.

I have invented and developed an effective skin treatment ointment that, in its broadest aspect, features a base containing petrolatum, beeswax or other wax, and antibiotic ingredient. This base can be combined with zinc oxide and an anti-itch ingredient for universal applicability to, and effective treatment of, normal skin disorders.

In another aspect, this invention comprises an ointment which comprises 5–10 parts petrolatum, 0.5–5 parts beeswax (or other wax), 0.25–5 parts antibiotic ingredient, In a further aspect, this invention features the optional addition of ½ part (or more) zinc oxide, and optional addition of ½ part (or more) hydrocortisone or other anti-itch agent.

These and other objects and features of this invention will become more readily apparent upon reference to the following detailed description of a preferred embodiment.

DESCRIPTION OF THE PREFERRED EMBODIMENT

As a result of my experimentations and trials, I found that a successful ointment needed moisturize the skin and seal in the moisture, yet enable the skin to breathe. The ointment needed to treat dry skin, rough red skin, cut skin, cracked and bleeding skin. Wax alone is a good sealer, but not an effective treatment, because it doesn't allow the skin to breathe. Petrolatum alone is a good moisturizer, but has a greasy feel and is easily rubbed off. However, in the right proportions, the combination of petrolatum and wax was found to be an effective moisturizer.

To treat cuts and lesions, I found readily available triple antibiotic ointment to be an effective ingredient. Many commercial versions of this are available and contain, e.g. Bacitracin 4000 units, Neomycin 3.5 mg and Polymixin B Sulfate 5000 units. In actual tests, this ingredient was effective, but it was found that the combination of all three antibiotics can cause some reddening of the skin for some highly allergic people. This was countered by using only the Bacitracin antibiotic component. To combat skin itching, varying amounts of hydrocortisone were used.

After testing a wide variety of combinations of elements, I found that an effective skin treatment ointment comprises:

Wax—0.5–5.0 parts

Petrolatum—4.0–10.0 parts

Antibiotic—0.25–5.0 parts

Zinc oxide—up to 8.0 parts

Anti-itch—up to 0.28 parts.

Although the amounts of specific ingredients can be increased or decreased to combat specific problems, my goal was to develop a skin treatment ointment that effectively treated a wide variety of common skin ailments, especially psoriasis. It was found that a general ointment containing all of these ingredients provided a universal ointment for the treatment of a variety of skin disorders of all degrees of severity. I tested ointments using varying amounts of these ingredients in the ranges above. Although some were more or less effective, depending on the skin ailment being treated, I found that the following preferred embodiment was the most universally effective in treating the vast assortment of skin aliments which plague people:

Wax—1.8 parts

Petrolatum—7.0 parts

Antibiotic—0.817 parts

Zinc oxide—0.4 parts

Anti-itch—0.05 parts.

Expressed in percentages, a specific formulation of a preferred formulation is:

Wax—18.0%

Petrolatum—69.8%

Neomycin antibiotic—0.00%

Polymyxin B Sulfate antibiotic—7.5%

Bacitracin antibiotic—0.6%

Zinc oxide—4.0%

Hydrocortisone anti-itch ingredient—0.5%.

A variety of skin disorders in a number of people of different types have been successfully treated by the preferred embodiment of skin treatment ointment of this invention. Causes of the skin disorders treated include harsh chemicals, temperature extremes, moisture extremes, cuts, bruises, natural irritants and rashes (such as poison ivy, oak and sumac), and other diseases, such as psoriasis and Fifth's disease. All of these, separately or in combination, produce painful and debilitating skin disorders, which include symptoms of dryness, itching, redness, rashes, bleeding and lesions.

The inventor suffered from severe psoriasis for many years, which produced very dry, cracked and bleeding skin on hands and arms. A variety of over-the-counter and prescription medications, lotions, ointments and creams were tried. Not only did they all fail to cure the skin disorder, many exacerbated the conditions. As a result, he sought to develop an effective ointment to treat himself. He finally developed the mixture of this invention, which he applied three times daily. After only two weeks of treatment, he was cured, with all lesions and cuts gone, and dryness alleviated. He has found that a daily morning maintenance application prevents recurrence and that use after experiencing skin abuse (e.g. after chemical exposure) prevents skin dryness. He has also found that the skin treatment ointment of this invention is effective as an after-shave lotion to combat shaving rash.

He then sought out other sufferers on whom to test his ointment. The results follow:

Case 1: Female adult suffering from severe persistent rash caused by poison ivy. Dermatologist prescribed valisone without success. Application of ointment only once per day completely healed subject in 2½ days.

Case 2: Female adult and female child suffered severe dry skin allergies, psoriasis for years. Ointment application caused allergic reaction to antibiotic, which was changed to a non-allergenic form of antibiotic (Bacitracin only). Treatment for 4 weeks cured skin disorders.

Case 3: Female adult suffered from painful, weeping lesions on hands, arms and legs. Treatment by a variety of skin specialists for six-year period failed to cure. Treatment with ointment three times daily for four weeks completely cured skin disorders.

Case 4: Elderly female suffered red, cracked and bleeding hands. Prior treatment with Vaseline and occlusion by cotton gloves at night. Change to application of ointment three times daily cured skin disorder after one week.

Case 5: Adult male house painter suffered from dry, irritated skin caused by contact with harsh chemicals. Treatment with ointment brought immediate relief.

Case 6: Adult male suffered dry, cracked and bleeding hands in winter. Treatment by various over-the-counter medications proved unsatisfactory. Treatment with ointment when needed relieves symptoms.

Case 7: Adult male suffering from 1st degree sunburn treated affected area with ointment. After several hours, all pain disappeared and redness turned to tan.

Case 8: Adult male developed allergic reaction to contact with garden plants. Rash significantly reduced several hours after treatment with ointment and disappeared next morning.

Case 9: Adult female suffering from red, irritated skin on legs disappeared after four treatments spaced two days apart.

Case 10. A variety of adult and minor males and females, Caucasian and black, who suffered from varying degrees of skin dryness have found that daily treatment with the ointment relieves all symptoms.

It has been found that the preferred treatment method is topical application to the affected area three times daily until healed, then once daily for maintenance of supple skin and prevention of reoccurrence. Such treatment has been found effective for the fill range of skin disorders discussed herein.

Although it is not fully understood as to why this ointment in any of its forms is so dramatically effective in curing these skin disorders, it is thought the constituent ingredients have a synergistic effect when used in combination. The ingredients in this ointment are thought to have the following functions. The petrolatum acts as a moisturizer, while the wax serves as a sealant to keep the treated skin area moisturized. Where there is a skin lesion or cut, the antibiotic is added to attack the infection. Zinc oxide promotes blood coagulation and sunburn or other burn healing, while the hydrocortisone inhibits itching. The proportions of ingredients is important.

It is preferable that all of the ingredients are available without prescription, i.e. over the counter. While beeswax is preferred, other waxes can be used, such as paraffin, mineral wax, wool wax alcohol and ceresin. Petrolatum in the form of pure white petroleum jelly is preferred. Any available triple or single antibiotic cream or ointment may be used as a component in this ointment, preferably without other additives being present.

While only a preferred embodiment has been described and shown, obvious modifications are contemplated within the scope of this invention, as defined by the following claims.

I claim:

1. An ointment for the treatment of human skin, consisting essentially of approximately: wax—20.0%; petrolatum—74.45%; antibiotic—1.05%; and zinc oxide—4.0%; anti-itch ingredient—0.5%.

2. An ointment for treatment of human skin, consisting essentially of:

wax—0.5–5.0 parts;

petrolatum—4.0–10.0 parts;

antibiotic—0.25–5.0 parts;

zinc oxide—0.1–8.0 parts;

anti-itch ingredient—0.01–0.28 parts.

3. The ointment of claim 2, consisting essentially of, approximately:
- wax—1.8 parts;
- petrolatum—7.0 parts;
- antibiotic—0.817 parts;
- zinc oxide—0.4 parts;
- anti-itch ingredient—0.05 parts.

4. The ointment of claim 2, consisting essentially of, approximately:
- wax—17.6%
- petrolatum—69.8%;
- Neomycin antibiotic—0.007%;
- Polymyxin B Sulfate antibiotic—7.5%;
- Bacitracin antibiotic—0.6%;
- zinc oxide—4.0%;
- Hydrocortisone anti-itch ingredient—0.5%.

5. A method of treating a skin disorder on an affected area of human skin characterized by reddened, chapped or cracked skin, comprising the steps of
   a. providing a mixture consisting essentially of: wax—0.5–5.0 parts; petrolatum—4.0–10.5 parts; antibiotic—0.25–5.0 parts; zinc oxide—0.1–8.0 parts, and
   b. applying said mixture to the affected area three times daily until all symptoms have disappeared.

6. The Method of claim 5, wherein the mixture additionally includes anti-itch ingredient—0.01–0.28 parts.

* * * * *